United States Patent [19]

Adam

[11] 4,060,614
[45] Nov. 29, 1977

[54] 6-SUBSTITUTED 3-NITROIMIDAZO[1,2,b]PYRIDAZINE FOR THE CONTROL OF HEMORRHAGIC COLITIS IN SWINE

[75] Inventor: Alberto Eilert Adam, Wayne, N.J.

[73] Assignee: American Cyanamid Company, Stamford, Conn.

[21] Appl. No.: 707,922

[22] Filed: July 22, 1976

[51] Int. Cl.$^2$ .................. A61K 31/50; A61K 31/54; A61K 31/535
[52] U.S. Cl. .................................. 424/250; 424/246; 424/248.4
[58] Field of Search ........................ 424/250, 248, 246

[56] References Cited

U.S. PATENT DOCUMENTS

| 3,711,613 | 1/1973 | Tomcufcik et al. | 424/250 |
| 3,725,407 | 4/1973 | Tomcufcik et al. | 424/250 |

Primary Examiner—Sam Rosen
Attorney, Agent, or Firm—H. G. Jackson

[57] ABSTRACT

This disclosure describes compositions of matter useful for the treatment and prophylaxis of hemorrhagic colitis in swine. It also describes methods for controlling and preventing hemorrhagic colitis in swine by administering to the animals a therapeutically effective amount of a 6-substituted 3-nitroimidazo[1,2-b]-pyridazine.

8 Claims, No Drawings

4,060,614

6-SUBSTITUTED 3-NITROIMIDAZO[1,2-b]PYRIDAZINE FOR THE CONTROL OF HEMORRHAGIC COLITIS IN SWINE

BACKGROUND OF THE INVENTION

The compounds of the present invention are described in the A. S. Tomcufcik et al. United States Letters Patents 3,725,407 issued Apr. 3, 1973; 3,828,041 issued Aug. 6, 1974 and 3,905,974 issued Sept. 16, 1975. The patentees describe methods for synthesizing 6-substituted 3-nitroimidazo[1,2-b]pyridazines and indicate that the compounds can be used to control amoebic and trichomonal infections in warm-blooded animals. No suggestion is made and it is not obvious from the disclosure that the stated compounds would be effective for the control of hemorrhagic colitis in swine.

BRIEF SUMMARY OF THE INVENTION

This invention is a method for treating hemorrhagic colitis in swine which comprises, administering to the animals a therapeutically effective amount of a compound having the formula:

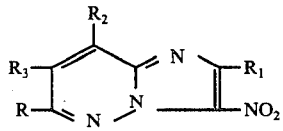

(I)

wherein R is hydroxy, mercapto, alkoxy ($C_1$-$C_8$), alkylthio ($C_1$-$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$-$C_8$) amino, dialkyl ($C_1$-$C_8$) amino, di(hydroxyloweralkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl or 4-diloweraminoloweralkyl-1-piperazinyl, sulfanilamido, alkyl ($C_1$-$C_4$)-sulfanilamido; thiomorpholino-S,S-dioxide; p-chlorobenzoyl hydrazido; p-chlorobenzylidene hydrazino; nicotinylidene hydrazino loweralkylthioloweralkoxy and loweralkylsulfonyloweralkoxy or —$NR_4$—CO—$R_5$ where $R_4$ is hydrogen or alkyl $C_1$-$C_4$ and $R_5$ is alkyl $C_1$-$C_{11}$, phenyl, 3,4-dichlorophenyl, 4-chloro-3-nitrophenyl, benzyl, mono and dihaloalkyl $C_1$-$C_4$ or 2-phenoxypropionamide; $R_1$ is hydrogen or alkyl $C_1$-$C_4$; $R_2$ and $R_3$ are hydrogen or methyl; and the pharmaceutically acceptable acid addition salts thereof. The invention also relates to therapeutic and prophylactic compositions containing a 6-substituted 3-nitro-imidazo[1,2-b]pyridazine which are useful for the control or prevention of hemorrhagic colitis in swine.

DETAILED DESCRIPTION OF THE INVENTION

Swine dysentery (bloody scours, hemorrhagic colitis) is one of the most destructive diseases encountered in swine husbandry. It is a widespread disease effecting all continents, and when observed in pigs it is generally characterized by one or more of the following symptoms: diarrhea, stunted growth, staggering gait, swelling of the eyelids, and coarseness of the hair. Although the severity of the disease varies from animal to animal, it nevertheless must be considered as one of the most important economic and clinical problems encountered in the rearing of swine. This is evidenced by the fact that dysentery infections in pigs generally result in 25% mortality of the herd and frequently produce 100% mortality. Moreover, diseased animals show a rapid loss of weight, and those cleared of the disease are subject to relapse and generally have a low market value.

In an attempt to overcome these difficulties and reduce losses due to the disease, a significant effort has been made by researchers throughout the world to determine the origin of the disease, to develop a means for preventing outbreaks of the disease in swine herds, and to provide an effective cure for animals. While these efforts have met with some success, there still remains much to be done in each of these areas. For example, the origin of swine dysentery has not yet been clearly determined, although several organisms, such as Treponema, Vibrio and Salmonella, have been found to be associated with outbreaks of the disease. Likewise, a plethora of prophylactic and therapeutic agents have been tested and have been found to be partially effective in reducing dysentery infections and/or curing infected animals. However, none of the treatments heretofore utilized have been entirely satisfactory even though such treatments have included a wide variety of drugs. Among the drugs utilized are the sulfa drugs, tetracycline antibiotics, mycin drugs, concentrated salines and alkalines, and arsenicals.

It is an object of this invention to provide a method for the prevention and/or cure of hemorrhagic colitis in swine by administering thereto, a prophylactic or therapeutic amount of a 6-substituted 3-nitroimidazo[2,1-b]pyridazine, as hereinafter described.

It is also an object of this invention to provide a method for controlling pathogenic anerobic organisms in homothermic animals by orally administering to the animals an effective amount of a 6-substituted 3-nitroimidazo[1,2-b]-pyridazine, as described below.

In accordance with this invention we have found a method for controlling hemorrhagic colitis in swine by orally administering to the host an effective amount (prophylactic or therapeutic) of a compound having the formula:

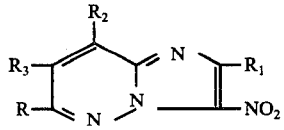

(I)

wherein R is hydroxy, mercapto, alkoxy ($C_1$-$C_8$) alkylthio ($C_1$-$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$-$C_8$) amino, dialkyl ($C_1$-$C_8$) amino, di(hydroxyloweralkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl 4-diloweraminoloweralkyl-1-piperazinyl, sulfanilamido, alkyl ($C_1$-$C_4$) sulfanilamido, 3-nitro-4-chlorobenzamido, thiomorpholino-S,S-dioxide, p-chlorobenzoylhydrazido, p-chlorobenzylidene hydrazino, nicotinylidene hydrazino, loweralkylthioloweralkoxy, loweralkylsulfonylloweralkoxy or —NR$_4$—CO—R$_5$ where R$_4$ is hydrogen, or alkyl C$_1$-C$_4$ and R$_5$ is alkyl C$_1$-C$_{11}$, phenyl, 4-chloro-3-nitrophenyl, benzyl, mono and dihaloalkyl (C$_1$-C$_4$) or 2-phenoxypropionamide; R$_1$ is hydrogen or alkyl C$_1$-C$_4$; R$_2$ and R$_3$ are hydrogen or methyl; and the pharmaceutically acceptable acid addition salts thereof.

A preferred group of compounds useful in the practice of the method of this invention have the formula:

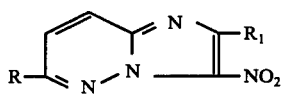
(II)

wherein R is hydroxy, mercapto, alkoxy (C$_1$-C$_8$), alkylthio (C$_1$-C$_8$) phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl (C$_1$-C$_8$) amino, dialkyl (C$_1$-C$_8$) amino, di(hydroxyloweralkyl)amino hydroxyloweralkylamino, lower alkoxyloweralkylamino, lower alkenylamino, phenylloweralkylamino, pyridylloweralkylamino, cycloalkyl (C$_3$-C$_6$) amino, diloweralkylaminoloweralkylamino, 1-piperidinyl, 1-pyrrolidinyl, 4-loweralkyl-1-piperazinyl, 4-lower alkoxyphenyl-morpholino, imidazolyl, 4-carboloweralkoxy-1-piperazinyl or 4-diloweraminoloweralkyl-1-piperazinyl, loweralkylthioloweralkoxy, loweralkylsulfonylloweralkoxy, R$_1$ is hydrogen or loweralkyl and a pharmaceutically acceptable acid addition salt thereof.

Another preferred group of compounds useful in the practice of this invention may be represented by the formula:

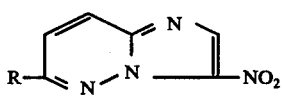
(III)

wherein R is sulfaniliamido; alkyl(C$_1$-C$_4$) sulfanilamido; 3-nitro-4-chlorobenzamido; thiomorpholino-S,S-dioxide; p-chlorobenzoyl hydrazido; p-chlorobenzylidene hydrazino; nicotinylidene hydrazino or —NR$_4$—CO—R$_5$ where R$_4$ is hydrogen or alkyl C$_1$-C$_4$ and R$_5$ is alkyl C$_1$-C$_{11}$, phenyl, 4-chloro-3-nitrophenyl, benzyl, mono or dihaloalkyl C$_1$-C$_4$, or 2-phenoxy-propionamide; and the pharmaceutically acceptable acid addition salts thereof.

Especially preferred compounds useful in this invention can be further defined as follows: (1) Formula II compounds wherein R$_1$ is hydrogen and R is 4-loweralkyl-1-piperazinyl, amino, alkoxy (C$_1$-C$_8$), diloweralkylaminoloweralkylamino, hydroxyloweralkylamino or imidazolyl; and (2) Formula III compounds where R is —Nr$_4$—CO—R$_5$, R$_4$ is hydrogen or methyl and R$_5$ is alkyl C$_1$-C$_{11}$, phenyl, 4-chloro-3-nitro-phenyl, benzyl, dichloromethyl or 2-phenoxypropionamide; and the pharmaceutically acceptable salts of both of the above defined formula II and III compounds.

Formula III compounds wherein R is sulfanilamido; alkyl (C$_1$-C$_4$) sulfanilamido; 3-nitro-4-chlorobenzamido; thiomorpholino-S,S-dioxide; p-chlorobenzoylhydrazido; p-chlorobenzylidene hydrazino; nicotinylidene hydrazino or —NH$_4$—CO—R$_5$ where R$_4$ is H or methyl and R$_5$ is phenyl, 4-chloro-3-nitrophenyl, benzyl, dichloromethyl or 2-phenoxypropionamide, can be prepared in accordance with the Tomcufcik et al. procedures U.S. Pat. No. 3,725,407 using the appropriate reactants. The procedure may be graphically illustrated as follows:

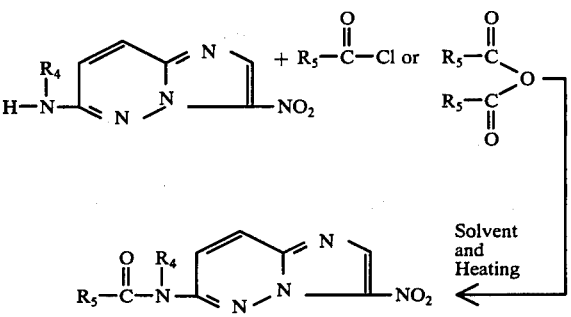

wherein R$_4$ and R$_5$ are as defined immediately above. These reactions are conducted under the conditions described by Tomcufcik et al.

We have found that a 6-substituted 3-nitroimidazo[1,2-b]pyridazine, as described above, is effective for the control of hemorrhagic colitis in swine when orally administered to infected host animals in amounts ranging from about 3.0 mg of about 100 mg per kilogram of body weight per day. A preferred dosage regimen for optimum results would be from about 10 mg of about 50 mg orally per kg of body weight per day. Such dosage units are employed that a total of from about 50 mg (for a 16 kg animal at 3.0 mg/kg) to about 10.0 grams (for a 100 kg animal at 100 mg/kg) of active ingredient are administered orally in a 24-hour period. The daily dosage may be administered as a single oral dose or as divided doses depending upon the exigencies of the therapeutic situation.

The dosage units of active compound may contain other inert or medically active materials, for instance, when the dosage unit form is a tablet, pill or granules, there may also be present various binders, fillers or solid diluents. Suitable materials for this purpose may be, for example, starch such as corn starch, or sugar as lactose or sucrose. When the dosage unit form is a capsule, it may contain in addition to materials of the above type a liquid carrier such as a fatty oil. The dosage unit form may also have present excipients such as dicalcium phosphate. Various other materials may be present as coatings or to otherwise modify the physical form of the dosage unit, for instance, pills or capsules may be coated with shellac, sugar or both. Of course, any material used in preparing the dosage unit form should be pharmaceutically pure and substantially non-toxic in the amounts employed.

Where the drug is to be administered as a single oral dose, for example in a therapeutic treatment, 5.25% by weight of the drug may be mixed with 4.25% by weight of hydroxystearin and 90.50% by weight of sesame oil. This formulation is administered by a syringe as an oral paste and will provide about 250 mg of drug per cubic centimeters (cc). It is, of course, obvious that a higher concentration of the drug can be achieved by altering the quantities of drug and sesame oil accordingly.

For phophylactic administration, the active ingredient is preferably administered either in the feed or in the drinking water at levels of from about 25 to about 500 parts per million, and preferably at levels of from 50 to 250 parts per million. This treatment is usually effective when administered over about a one-day to two-weak period, although the treatment period may be extended if so desired. For prophylactic or therapeutic treatment of animal via feed treatment, any conventional animal feed may be employed.

As indicated above, the 6-substituted-3-nitroimidazo[1,2-b]pyridazine is normally administered to the swine intimately mixed in the feed ration or drinking water for prophylaxis. The drug can be suitably prepared as a premix or feed supplement containing from about 1% to about 90% by weight of the formulation which can also contain various diluents or carriers. Carriers suitable for use to make up the feed supplement compositions include the following: soybean meal, alfalfa meal, cotton seed oil meal, linseed oil meal, cornmeal, cane molasses, urea, bone meal, corncob meal, dried fermentation whole mash solids, and the like. The carrier promotes a uniform distribution of the drug in the finished feed with which the supplement is blended. It thus performs an important function by ensuring proper distribution of the drug throughout the feed. The feed supplement or premix containing the active ingredient can be readily mixed with the feed ration by any conventional technique for mixing feeds. For convenience in commercial use, it has been found that premixes containing from about 5% to about 15% by weight of the active compound are preferred. When administering the compound in drinking water, it has been found convenient to utilize water-soluble excipients, e.g., lactose, dextrose, tartaric acid. The powder can be added to drinking water to provide an effective concentration level of active compound of from about 0.0025% to about 0.05% by weight.

Also in accordance with this invention, we have found that the above-identified swine dysentery, control agents can be used in combination with other drugs, such as anti-bacterial agents, antifungal agents, growth promoting agents, and the like, normally used in the raising of said animals.

For a clearer understanding of this invention, specific examples of it are set forth below. These examples are merely illustrative, and are not to be understood as limiting the scope and underlying principles of the invention in any way.

EXAMPLE 1

This experiment was conducted to determine the efficacy of 200, 100 and 50 g per ton of feed of 3-nitro-6-propoxyimidazo[1,2-b]pyridazine in preventing the occurrence of swine dysentery in experimentally infected weanling pigs. 3-Nitro-6-propoxyimidazo[1,2-b]pyridazine has been found effective in vitro against *Treponema hyodysenteriae*, one of the primary etiological agents of swine dysentery.

Weanling pigs (9 kg) were experimentally infected via feed with scrapings and contents of dysenteric colons. Medication with 200, 100 or 50 g of 3-nitro-6-propoxyimidazo[1,2-b]pyridazine per ton of feed was begun on the day after infection and continued for 3-weeks. The experiment was terminated at 5 weeks postinfection. The 200 and 100 g levels of the above-said pyridazine prevented mortality, maintained performance and completely prevented symptoms of swine dysentery. All infected, non-medicated pigs died with mucohemorrhagic colitis. Medication with 50 g of the pyridazine reduced mortality 40 percent and permitted no significant reduction in overall performance when compared to other medicated groups.

In these tests 50 Hampshire X Yorkshire Crossbred pigs (22 females, 28 castrated males), 5 to 6 weeks of age and weighing approximately 9.0 kg were weighed and tagged 16 days before infection. Seven days later they were randomly allotted by weight and sex to 10 pens of 5 pigs each. The pigs were weighed again the day before infection, and their feed was removed. Twenty hours later they were given nonmedicated feed mixture with phosphate buffered saline (PBS) 0.1 m, pH 7.0 or PBS plus scrapings and contents from the colons of dysenteric pigs. The pigs consumed the infective material within 1 hour, and nonmedicated feed was returned at the time. Medicated feed was given to groups C, D and E from day 1 through day 21. Nonmedicated feed was given to all pigs from days 21 to day 35.

| Composition of Swine Grower Ration Employed in These Tests | |
|---|---|
| Ingredients | % |
| Ground corn | 78.00 |
| Soybean meal | 17.50 |
| Meat and bone meal | 2.50 |
| Dicalcium phosphate | 0.75 |
| Iodized salt | 0.50 |
| Limestone | 0.60 |
| Vitamin premix 1/ | 0.075 |
| Mineral premix 2/ | 0.075 |
| | 100.000 |

1/ Furnished the following vitamins per ton of feed:
| | | |
|---|---|---|
| Vitamin A | 3,000,000 | IU |
| Vitamin $D_2$ | 600,000 | IU |
| Riboflavin | 6 | g |
| Pantothenic acid | 15 | g |
| Niacin | 30 | g |
| Vitamin $B_{12}$ | 15 | mg |
| Menadione (Source of Vitamin K) | 3 | g |
| Vitamin E | 7,500 | IU |
| Choline | 150 | g |

2/ Furnished the following minerals per ton of feed:
| | |
|---|---|
| Iron | 75 ppm |
| Copper | 7.5 ppm |
| Manganese | 45 ppm |
| Zinc | 75 ppm |

Results and Discussion

The infected, nonmedicated pigs (group B) first developed moderate to severe muco-hemorrhagic diarrhea on the 4th day postinfection. By day 7 all of the group B pigs were scouring severely, and the scouring continued at this level until day 21 when the last pig died. Mortality in group B, which occured between days 8 to 21 postinfection, reached 100 percent with a mean survial time of 11.7 days. T hyodysenteriae was observed in the colonic contents of all 10 pigs. The vibrio-like organisms were seen in 2 pigs, while only 1 pig was positive for the small spirochete. No Salmonella were isolated from the small or large intestines. Pathology in the stomachs included congestion, hyperemia, hemorrhage and ulcers. Necrosis or hemorrhagic necrosis was seen in all large intestines but one. No lesions were seen in the small intestines. The pigs medicated with 50 g of the pyridazine per ton of feed (group E) first developed severe mucohemorrhagic diarrhea (3 of 10) on day 6. The severe scouring reached a peak on day 11 (6 of 10), declined during the next 2 days, and then ceased on day 14. A second period of severe scouring began on day 19, reached a peak on day 22 (4 of 7), declined during the next 5 days, and then ceased on day 28. No severe scouring occurred during the last week of the experiment. Mortality in group E, which occurred between days 13 to 26, reached 60 percent with a mean survival time of 20 days (Table III, page 1853). *T. hyodysenteriae* was observed in the colonic contents of all 6 pigs. The vibriolike organisms were seen in 3 pigs, and the small spirochete was found in only 1 pig. No Salmonella were isolated from the intestines. Hyperemia, hemorrhage, hemorrhagic necrosis, or ulcers were seen in the stomachs of 5 of the 6 pigs. Catarrhal inflamation, hemorrhage or hemorrhagic necrosis were found in the colons of 5 of the 6 pigs. No lesions were seen in the small intestines.

The 4 surviving group E pigs were sacrificed after termination of the experiment. *T. hyodysenteriae* and the small spirochete were not detected, and vibrio-like organisms were seen in only one pig. No Salmonella were isolated, and no lesions were found in the gastrointestinal tract. None of the pigs in the groups medicated with 200 (group C) or 100 (group D) grams of imidazo[1,2-b]pyridazine, 3-nitro-6-propoxy- per ton of feed developed symptoms of dysentery. No severe scours were seen throughout the experiment.

None of the pigs in groups C and D died from swine dysentery. One pig in group C (200 g pyridazine/ton) died on day 20 with pneumonic lungs, a mottled and congested liver, and mucoid enteritis in the small intestine. A β-hemolytic, coagulase-negative staphylococcus was isolated from the lungs, and an *E. coli* was isolated from the liver. No lesions were seen in the large intestine and no spirochetes (*T. hyo.*) were observed. Salmonella were not isolated from the small or large intestines. The pig that died had no fever days, but it lost 2 pounds during the second week post-infection and was practically moribund during the week before it died.

The 19 surviving pigs in groups C and D were sacrificed after termination of the experiment. *T. hyodysenteriae* was observed in occasional microscopic fields in one pig from each group. The small spirochete was seen in 3 pigs and the vibrio-like organism in 5 pigs. No Salmonella were isolated from the intestines. Hyperemia was seen in the stomach of 2 group C pigs, but no lesions were found in the intestines. None of the group D pigs had lesions in the stomach and small intestine, and only 2 pigs had mild pathology in the large intestine.

Some light scouring occurred in the noninfected group of pigs (group A) throughout most of the experiment. Occasionally some moderate scouring also was seen, but the stools never contained blood or mucus. Fecal samples were taken on day 14 and cultured for Salmonella, but none was isolated.

One pig in group A died on day 22 postinfection. The lungs were pneumonic and the pleural cavity was filled with fluid; a β-hemolytic coagulase-negative staphylococcus was isolated from the lungs. The peritoneal cavity also was filled with fluid and mucoid enterities was seen in the small intestine. No spirochetes and no lesions were observed in the large intestine. No Salmonella were isolated from the large or small intestines. The pig that died had 6 fever days out of a possible total of 21, and it failed to gain weight during the third week postinfection.

Average daily gain, average daily feed consumption and average feed efficiency for all treatment groups is reported in Table I below.

Table I

| Swine Dysentery Evaluation | | | | | |
|---|---|---|---|---|---|
| | Group | | | | |
| Infection | A | B | C | D | E |
| 3-Nitro-6-propoxyimidaze[1,2-b]pyridazine(ppm) | − | + | + | + | + |
| | 0 | 0 | 220 | 110 | 55 |
| Average Initial Weight (kg) | 9.0 | 8.8 | 9.0 | 10.0 | 8.3 |
| Number of survivers/Total | 9/9 | 0/10 | 9/9 | 10/10 | 4/10 |
| Mean Survival Time (days) | — | 11.7 | — | — | 20.0 |
| Average Daily Gain (kg/pig) | | | | | |
| 0–1 Week | 0.20 | −0.11 | 0.07 | 0.14 | 0.11 |
| 0–2 Weeks | 0.17 | 0.14 | 0.23 | 0.22 | 0.07 |
| 0–3 Weeks | 0.19 | — | 0.25 | 0.27 | 0.07 |
| 0–4 Weeks | 0.25 | — | 0.30 | 0.32 | 0.12 |
| 0–5 Weeks | 0.34 | — | 0.37 | 0.37 | 0.18 |
| Average Daily Feed Consumption (kg/pig) | | | | | |
| 0–1 Week | 0.37 | 0.26 | 0.36 | 0.35 | 0.30 |
| 0–2 Weeks | 0.43 | 0.20 | 0.48 | 0.50 | 0.30 |
| 0–3 Weeks | 0.51 | 0.16 | 0.57 | 0.62 | 0.33 |
| 0–4 Weeks | 0.62 | — | 0.65 | 0.69 | 0.38 |
| 0–5 Weeks | 0.74 | — | 0.76 | 0.80 | 0.46 |
| Average Feed Efficiency (kg/kg) | | | | | |
| 0–1 Week | 2.06 | — | 4.84 | 2.82 | 2.86 |
| 0–2 Weeks | 2.48 | — | 2.12 | 2.26 | 4.12 |
| 0–3 Weeks | 2.80 | — | 2.23 | 2.33 | 4.47 |
| 0–4 Weeks | 2.56 | — | 2.20 | 2.14 | 3.21 |
| 0–5 Weeks | 2.21 | — | 2.07 | 2.16 | 2.57 |

Underlined value represent one pen only.

EXAMPLE 2

Control of Hemorrhagic Colitis in Siwne

The procedure of Example 1 is repeated using 50 different Hamsphire X Yorkshire Crossbred weanling pigs. Data obtained are similar to that obtained in Example 1. Such data are reported in Table II below.

Table II

| Swine Dysentery Evaluation | | | | | | |
|---|---|---|---|---|---|---|
| | Group | | | | | |
| Infection | A | B | C | D | E | F |
| 3-Nitro-6-Propoxyimidaze[1,2-b]pyridazine g/T | 0 | + 0 | + 100 | + 75 | + 50 | + 0 |
| Dimetridazole (g/ton) | 0 | 0 | 0 | 0 | 0 | 50 |
| Avg. Initial Weight (kg) | 13.0 | 13.1 | 13.2 | 13.0 | 12.4 | 12.4 |
| Morbidity | 0/10 | 8/10 | 0/10 | 0/10 | 1/10 | 3/10 |

Table II-continued

Swine Dysentery Evaluation

| Infection | Group A | B | C | D | E | F |
|---|---|---|---|---|---|---|
| Mortality | 1/10* | 9/10* | 1/10* | 0/10 | 1/10 | 2/10 |
| Average Daily Gain (kg/pig) | | | | | | |
| 0-1 Week | 0.32 | −0.06 | 0.38 | 0.34 | 0.28 | 0.16 |
| 0-2 Weeks | 0.38 | 0.00 | 0.44 | 0.38 | 0.28 | 0.38 |
| 0-3 Weeks | 0.45 | 0.23 | 0.48 | 0.42 | 0.35 | 0.45 |
| 0-4 Weeks | 0.48 | 0.24 | 0.53 | 0.46 | 0.38 | 0.48 |
| 0-5 Weeks | 0.52 | 0.25 | 0.55 | 0.49 | 0.44 | 0.51 |
| Average Daily Feed Consumption (kg/pig) | | | | | | |
| 0-1 Week | 0.78 | 0.54 | 0.82 | 0.82 | 0.64 | 0.64 |
| 0-2 Weeks | 0.94 | 0.53 | 0.96 | 0.94 | 0.80 | 0.85 |
| 0-3 Weeks | 1.08 | 0.80 | 1.07 | 1.04 | 0.94 | 1.00 |
| 0-4 Weeks | 1.17 | 0.91 | 1.16 | 1.14 | 1.05 | 1.10 |
| 0-5 Weeks | 1.26 | 0.91 | 1.30 | 1.24 | 1.16 | 1.19 |
| Average Feed Efficiency (kg/kg) | | | | | | |
| 0-1 Week | 2.46 | 11.17 | 2.18 | 2.70 | 2.29 | 4.88 |
| 0-2 Weeks | 2.50 | 6.00 | 2.22 | −2.53 | 2.83 | 2.20 |
| 0-3 Weeks | 2.41 | 3.48 | 2.20 | 2.48 | 2.69 | 2.22 |
| 0-4 Weeks | 2.41 | 3.79 | 2.20 | 2.51 | 2.76 | 2.30 |
| 0-5 Weeks | 2.45 | 3.64 | 2.36 | 2.54 | 2.68 | 2.33 |

*One pig died from causes unrelated to dysentery.
Underlined values represent one pen only.

EXAMPLE 3

Control of *Treponema hyodysenteriae* with a 6-substituted 3-nitroimidazo[1,2-b]pyridazine Three strains of *Treponema hyodysenteriae* were obtained and utilized in these evaluations. The Treponemas were grown on trypticase soy agar supplemented with 5% sheep red blood cells. Blocks (2×3 cm) or plugs (2 mm) of agar were cut out from hemolytic areas of mature cultures and placed upon or streaked over fresh agar plates. The inoculated plates were placed in anerobic jars which were then evacuated and filled twice with carbon dioxide and finally evacuated and filled with 80% hydrogen plus 20% carbon dioxide. The plates were incubated at 37° C for 3 to 4 days. Then, before inoculation plates were incubated at 25° C for 3 to 4 days in the hydrogen-carbon dioxide atmosphere.

Test drugs were dissolved in dimethyl sulfoxide (DMSO) to a concentration of 10,000 mcg/ml. Ten fold serial dilutions were made to DMSO to a concentration of 0.01 mcg/ml, where necessary. The solutions (0.05 ml) were applied twice to highly absorbant paper discs (6.35 mm diameter), and the disc were incubated at 60° C for approximately 3 hours following each application. If not used immediately, the discs were stored in petri plates at 8° C.

Agar plates were streaked heavily with plugs of hemolytic agar from 3 to 4 day old cultures. Up to four discs were placed on each 100 mm diameter plate and the plates were incubated in anaerobic jars as described previously. DMSO control discs were included for each strain. After 3 to 4 days of incubation the inhibition of growth (hemolysis) was determined. Increasing dilutions (lower concentrations) were tested until no inhibition was found. The highest dilution that was active was then retested to confirm its activity and tests with each strain were repeated until a conclusive result was obtained. Data obtained are reported in Table III below where the lowest effective level for complete control of all strains of Treponema is reported for each compound evaluated.

Table III

Lowest Effective Concentration (mcg) of Test Compound Giving Complete Control of all 3 Stains of *Treponema* Used for Evaluation

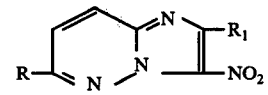

| R | $R_1$ | Effective Level of Compound in (mcg) for Treponema Control |
|---|---|---|
| $OC_2H_5$ | H | 1.0 |
|  | H | 0.01 |
| −N⟨ ⟩N−CH₃ | | |
| $OCH_3$ | $CH_3$ | 1.0 |
| $NH_2$ | H | 0.01 |
| Cl | $CH_3$ | 1.0 |
| −N(CH₃)₂ | $CH_3$ | 1.0 |
| NH−CO−CH₃ | H | 0.01 |
| −N(C₄H₉)₂ | H | 0.1 |
|  | H | 0.1 |
| −N⟨ ⟩O | | |
| −N−CH₂C₆H₅ <br> \| <br> CH₃ | H | 0.1 |
| −N(CH₂CH₂OH)₂ | H | 0.1 |
|  | H | 0.1 |
| −N⟨ ⟩ | | |
| −N(CH₃)(C₄H₉) | H | 1.0 |
|  | H | 0.1 |
| −N⟨ ⟩N−CO₂−C₂H₅ | | |
| −NH(CH₂)₂N(C₂H₅)₂ · HCl | H | 0.01 |
| −NH(CH₂)₃N(CH₃)₂ | H | 0.1 |
|  | H | 0.1 |
| −NHCH₂−⟨pyridyl⟩ | | |
| −NHC₈H₁₇ | H | 0.1 |
|  | H | 0.1 |
| −NH−NH−CO−⟨C₆H₄⟩−Cl | | |

Table III-continued

Lowest Effective Concentration (mcg) of Test Compound Giving Complete Control of all 3 Stains of *Treponema* Used for Evaluation $$R\text{---}\underset{N}{\overset{N}{\diagdown}}\text{---}\overset{N}{=}\underset{NO_2}{\overset{R_1}{\diagup}}$$

| R | $R_1$ | Effective Level of Compound in (mcg) for *Treponema* Control |
|---|---|---|
| —N⁺(CH₃)₃O₃S—⟨C₆H₄⟩—CH₃ | H | 1.0 |
| —N(piperazinyl)N—(CH₂)₃—N(CH₃)₂ . 2HCl | H | 0.1 |
| —N(—C₈H₁₇ . HCl)CH₃ | H | 0.1 |
| —NH—CH₂C₆H₅ | H | 0.1 |
| —OCH₂C₆H₅ | H | 1.0 |
| ⟨3,4-dichlorophenyl⟩ | H | 1.0 |
| —NH—CH(C₂H₅)—CH₂OH | H | 0.01 |
| | H | 0.01 |
| NHN=CH—⟨C₆H₄⟩—Cl | H | 0.01 |
| —NH—CO—C₆H₅ | H | 0.01 |
| OCH₂CH₂OC₂H₅ | H | 0.1 |
| O—CH₂—CH₂OCH₃ | H | 0.1 |
| OCH₂CH₂SO₂C₂H₅ | H | 0.1 |
| OCH₂CH₂SC₂H₅ | H | 0.1 |
| —OCH₂—COOC₂H₅ | H | 0.01 |
| NH—N=CH—⟨pyridyl⟩ | H | 0.01 |
| —N(—CO—CH₃)CH₃ | H | 0.01 |
| —OCH₂CH=CH₂ | H | 0.1 |
| | H | 0.1 |
| —OCH₂—CO—⟨C₆H₄⟩—Cl | | |
| —NH—CO—C₂H₅ | H | 0.01 |
| —OCH₂CH₂N(CH₃)₂ . HCl | H | 0.1 |
| —OCH₂CH₂OH | H | 0.1 |
| —OC₈H₁₇ | H | 0.1 |
| OCH₂CH₂—N(phthalimido) | H | 0.1 |
| —N(thiomorpholino-SO₂)— | H | 0.1 |
| —NH—CO—CH₂C₆H₅ | H | 0.01 |
| —NH—CO—C₁₁H₂₃ | H | 0.1 |
| —NH—COCHCl₂ | H | 0.01 |
| —N(piperazinyl)NH | H | 0.1 |
| —NH—CO—CH(OC₆H₅)—CH₃ | H | 0.1 |
| OC₃H₇ | H | 1.0 |
| —NH—SO₂—⟨C₆H₄⟩—NH₂ | H | 1.0 |
| —NH—SO₂—CH₃ | H | 1.0 |

I claim:

1. A method of treating hemorrhagic colitis in swine which comprises, administering to the animals a therapeutically effective amount of a compound having the formula:

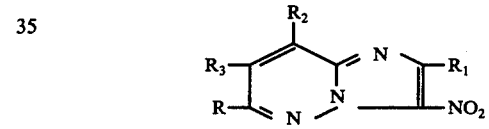

wherein R is hydroxy, mercapto, alkoxy ($C_1$-$C_8$), alkylthio ($C_1$-$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$-$C_8$) amino, dialkyl ($C_1$-$C_8$) amino, di(hydroxyloweralkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl or 4-diloweraminoloweralkyl-1-piperazinyl, sulfanilamido, alkyl ($C_1$-$C_4$)-sulfanilamido; thiomorpholino-S,S-dioxide; p-chlorobenzoyl hydrazido; p-chlorobenzylidene hydrazino; nicotinylidene hydrazino loweralkylthioloweralkoxy and loweralkylsulfonyloweralkoxy or —NR₄—CO—R₅ where R₄ is hydrogen or alkyl $C_1$-$C_4$ and R₅ is alkyl $C_1$-$C_{11}$, phenyl, 3,4-dichlorophenyl, 4-chloro-3-nitrophenyl, benzyl, mono and dihaloalkyl $C_1$-$C_4$ or 2-phenoxypropionamide; $R_1$ is hydrogen or alkyl $C_1$-$C_4$; $R_2$ and $R_3$ are hydrogen or methyl; and the pharmaceutically acceptable acid addition salts thereof.

2. A method according to claim 1 wherein the compound has the formula:

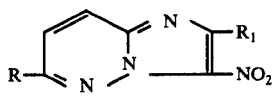

wherein R is hydroxy, mercapto, alkoxy ($C_1$-$C_8$) alkylthio ($C_1$-$C_8$), phthalimidoloweralkoxy, phenylloweralkoxy, lower alkylaminoloweralkoxy, lower alkoyloweralkoxy, hydroxyloweralkoxy, lower alkenyloxy, hyhalobenzoylloweralkoxy, amino, alkyl ($C_1$-$C_8$) amino, dialkyl ($C_1$-$C_8$) amino, di(hydroxylower-alkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl or 4-diloweraminoloweralkyl-1-piperazinyl lower alkylthioloweralkoxy, lower alkylsulfonylloweralkoxy; $R_1$ is hydrogen or loweralkyl and a pharmaceutically acceptable acid addition salt thereof.

3. A method according to claim 1 wherein the compound has the formula:

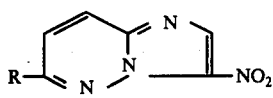

where R is sulfanilamido, alkyl($C_1$-$C_4$)sulfanilamido, 3-nitro-4-chlorobenzamido, thiomorpholino-S,S-dioxide, p-chlorobenzoyl hydrazido, p-chlorobenzylidene hydrazino, nicotinylidene hydrazino or —$NR_4$—CO—$R_5$ where $R_4$ is hydrogen or alkyl $C_1$-$C_4$ and $R_5$ is alkyl $C_1$-$C_{11}$, phenyl, 4-chloro-3-nitrophenyl, benzyl, mono or dihaloalkyl $C_1$-$C_4$ or 2-phenoxypropionamide and the pharmaceutically acceptable acid addition salts thereof.

4. A method according to claim 2 wherein $R_1$ is hydrogen and R is 4-loweralkyl-1-piperazinyl, amino, alkoxy $C_1$-$C_8$, diloweralkylaminoloweralkylamino, hydroxyloweralkylamino or imidazolyl and the pharmaceutically acceptable salts thereof.

5. A method according to claim 3 wherein R is —$NR_4$—CO—$R_5$; $R_4$ is hydrogen or methyl and $R_5$ is alkyl $C_1$-$C_{11}$, phenyl, 4-chloro-3-nitrophenyl, benzyl, dichloromethyl or 2-phenoxypropionamide and the pharmaceutically acceptable salts thereof.

6. A method according to claim 1 wherein the compound is 3-nitro-6-propoxyimidazo[1,2-b]pyridazine.

7. A method according to claim 1 for treating hemorrhagic colitis in swine which comprises administering orally to the swine a 6-substituted-3-nitroimidazo[1,2-b]-pyridazine according to claim 1 in association with a pharmaceutical carrier to provide a daily dosage of the pyridazine of from about 3.0 mg to about 100 mg per kg of body weight of the swine.

8. The method for controlling and preventing hemorrhagic colitis in swine which comprises administering in a prophylactically effective amount to the swine an oral ration containing from about 25 parts to about 500 parts per million parts of ratio of a 6-substituted 3-nitroimidazo[1,2-b]-pyridazine according to claim 1.

* * * * *